United States Patent [19]
Collins

[11] Patent Number: 5,512,557
[45] Date of Patent: Apr. 30, 1996

[54] CORONARY HEART DISEASE TREATED WITH 17βOESTRADIOL

[75] Inventor: Peter Collins, Richmond, England

[73] Assignee: National Heart and Lung Institute, London, England

[21] Appl. No.: 132,369

[22] Filed: Oct. 7, 1993

[51] Int. Cl.⁶ ................................................. A61K 31/56
[52] U.S. Cl. ........................ 514/182; 514/170; 514/171; 514/178
[58] Field of Search ................................. 514/170, 171, 514/178, 182

[56] References Cited

PUBLICATIONS

Godsland, I. F., et al., "Sex, plasma lipoproteins, and atherosclerosis: Prevailing assumptions and outstanding questions," American Heart Journal: vol. 114, No. 6, pp. 1467–1503 (Dec. 1987).
Rosano Giuseppe M. C., et al., "Beneficial effect of estradiol 17–bet on exercise–induced myocardial ischaemia in woman with coronary arter disease. A double blind randomized placebo controlled study" J. Am Coll. Cardiol., vol. 21, No. 2, Suppl. A). pp. 64A, 1993. 42nd Ann. Scientific Session of the Am. Coll. of Cardiology (Mar. 14–18 1993).
Rosano, Giuseppe M. C., et al., "Beneficial effect of oestrogen on exercise–induced myocardial ischaemia in woman with coronary artery disease," The Lancet, vol. 342, pp. 133–136 (Jul. 17, 1993).
Bain, Christopher, et al., "Use of Postmenopausal Hormones and Risk of Myocardial Infarction," Circulation, vol. 64, No. 1, pp. 42–(1981).
Barr, David P. et al. "Influences of Estrogen on Lipoproteins in Atherosclerosis" Trans. Assoc. Am. Physicians, 1952, 65:102.
Colditz, Graham A. et al., "Menopause and the Risk of Coronary Heart Disease in Women," The New England Journal of Medicine, vol. 316, No. 18, pp. 1105–1110 (1987).
Gordon, Tavia, et al., "Menopause and Coronary Heart Disease," Annals of Internal Medicine, vol. 89, No. 2, pp. 167–161 (1978).
Hammond, Charles B., "Effects of long–term estrogen replacement therapy," Am J. Obstet Gynecology, vol. 133, No. 5, pp. 525–536 (1979).
Petitti, Diana B., et al. "Risk of Vascular Disease in Women," JAMA, vol. 242, No. 11, pp. 1150–1154 (1979).
Pfeffer, R. I., et al., "Coronary Risk and Estrogen Use in Postmenopausal Woman," American Journal of Epidemiology, vol. 107, No. 6, pp. 479–487 (1978).
Rosenberg, Lynn, et al. "Myocardial Infarction and Estrogen Therapy in Post–Menopausal Women," The New England Journal of Medicine, vol. 294, No. 23, pp. 1256–1259 (1976).
Rosenberg, Lynn, et al., "Noncontraceptive Estrogens and Myocardial Infarction in Young Women," JAMA, vol. 244, No. 4, pp. 339–342 (1980).
Ross, Ronald K., et al. "Menopausal Oestrogen Therapy and Protection from Death from Ischaemic Heart Disease," The Lancet, Apr. 18, 1981, pp. 858–860.
Stampfer, Meir J. et al. "A Prospective Study of Postmenopausal Estrogen Therapy and Coronary Heart Disease," The New England Journal of Medicine, vol. 313, No. 17, pp. 1044–1049 (1985).
Szklo, Moyses, et al. "Estrogen Use and Myocardial Infarction Risk: A Case–Control Study," Preventive Medicine, vol. 13, pp. 510–516 (1984).
Wilson, W. F., et al. "Postmenopausal Estrogen Use, Cigarette Smoking, and Cardiovascular Morbidity in Woman Over 50," The New England Journal of Medicine, vol. 313, No. 17, pp. 1038–1043 (1985).
American Heart Association, "Supplement to Circulation vol. 86, No. 4 Oct. 1992, p. I–537, abst 2137, Abstracts from the 65th Scientific Session," (Nov. 16–19, 1992).
Bush, Trudy L., et al., "Cardiovascular mortality and non-contraceptive use of estrogen in women: results from the Lipid Research Clinics Program Follow–up Study," Circulation, vol. 75, pp. 1102–1109 (1987).
Colditz, Graham A., et al., "Menopause and the Risk of Coronary Heart Disease in Women," The New England Journal of Medicine, vol. 316, No. 8, pp. 1105–1110 (1987).
Earl R. Plunkett, et al; Amer. J. Obstet Gynecol. Jan., 1992, pp. 117–121.

Primary Examiner—Theodore J. Criares
Attorney, Agent, or Firm—Louis Myers

[57] ABSTRACT

Use of 17β-oestradiol in the treatment of coronary heart disease.

3 Claims, No Drawings

CORONARY HEART DISEASE TREATED WITH 17β OESTRADIOL

The present invention relates to the treatment of coronary heart disease and provides a pharmaceutical composition for such treatment, as well as a method for the treatment of coronary heart disease.

BACKGROUND OF THE INVENTION

Coronary heart disease arises from damage to the cardiac muscle, the myocardium, caused by insufficient flow of blood in the coronary arteries. The reduced flow of blood is termed myocardial ischemia, and the resulting heart damage is reflected in severe attacks of pain known as angina pectoris. The attacks of pain may be relieved or prevented using drugs, for example by sublingual administration of nitroglycerin or by the oral use of β-blocking agents and calcium antagonists. Apart from relieving or preventing the angina, coronary heart disease may be treated by a combination of further methods, including the use of other drugs and the use of surgery.

Coronary heart disease is particularly prevalent in women who have past the time of menopause. Furthermore, an increase in the incidence of heart conditions, including coronary artery disease, angina pectoris and vasomotor disturbance, is associated with the menopause.

SUMMARY OF THE INVENTION

The present invention provides compositions and methods for the therapeutic treatment of coronary heart disease. Such compositions and methods are based on the discovery that an oestrogen improves exercise-induced myocardial ischaemia in female patients with coronary artery disease.

Thus, the present invention provides a pharmaceutical composition for treatment of coronary heart disease, comprising a synthetic or natural oestrogen together with a pharmaceutically acceptable carrier.

Correspondingly, a method for the treatment of coronary heart disease, especially coronary heart disease in post-menopausal women, comprises administration of an effective amount of an oestrogen. The treatment will generally be chronic but acute treatment is possible. The compositions can readily be formulated and administered to suit the mode of treatment.

Other features and advantages of the invention will be apparent from the following description and the claims.

PREFERRED EMBODIMENTS OF THE INVENTION

The currently preferred oestrogen is 17β-oestradiol. Another product which may be employed is one prepared from the urine of pregnant mares, such as that sold by Wyeth under the Trade Name "Premarin" and which comprises a number of oestrogens, not all identified.

In a particularly preferred embodiment, the method of treatment of the present invention comprises the steps of:
diagnosing coronary heart disease in a patient; and then
administering to said patient an effective amount of an oestrogen. The patient can then be monitored for improvement in the heart condition.

Typically the patient, a male of, say, 40 to 60 years or a female of, say, 60 to 75 years will exhibit one or more of the symptoms of coronary heart disease, including exceptional chest pain and shortness of breath. The oestrogen can be administered in various forms, depending upon the patient and the desired route of administration which may be oral, parenteral or transdermal. Suitable formulations for oral administration include tablets, capsules, granules, powders or syrups; and suitable formulations for parenteral administration include injections (which may be intravenous, intramuscular or subcutaneous), drops or suppositories. These various formulations can be prepared by conventional means in which the oestrogen is mixed with additives such as those commonly employed in the field of pharmaceutical preparations, including vehicles, binders, disintegrators, lubricants, corrigents, solubilizers, suspending agents and coating agents. Similarly the active ingredient may be formulated as a skin patch for transdermal application, e.g. the product Estradern manufactured by Ciba Laboratories.

The dosage may be varied depending on the symptoms, age and body weight of the patient, the route of administration and the form of the preparation. A daily dose of from 0.1 mg to 10 mg, more typically 0.5 mg to 2 mg, which may be administered in a single dose or in divided doses, is usually appropriate for an adult human patient. For female patients, if the uterus is intact, the oestrogen may be administered in conjunction with added progesterone from 14–28 days.

The present invention also provides for the use of an oestrogen in the manufacture of a medicament for the treatment of coronary heart disease, and particularly of coronary heart disease and myocardial ischaemia in female patients, particularly menopausal and post-menopausal women.

Oestrogens have previously been administered for several medical indications, notably in hormone replacement therapy for menopausal and postmenopausal women. However, stemming from a recognition of the adverse effects of the contraceptive pill, the administration of oestrogens is contra-indicated for patients with coronary heart disease, and the pharmacopoeia contain warnings for oestrogen products that they are not to be given to patients with cardiac disease. Thus, no medical practitioner will prescribe oestrogen for a patient with coronary heart disease.

Ovarian hormones, and in particular 17β-oestradiol, are vasoactive substances. They have been shown to increase cardiac output and arterial flow velocity, and decrease vascular resistance, systolic and diastolic blood pressure (see, for example, Am. Heart J. 1987; 114: 1467–1503; N. Engl. J. Med. 1987; 316; 1105–1110; and .Circulation 1987; 75:1102–1109).

EXAMPLES OF THE INVENTION

The present invention is exemplified but not limited by the following Examples.

Example 1

The acute effect of sublingual 17β-oestradiol on exercise-induced myocardial ischaemia was assessed in women with coronary artery disease.

The study population consisted of 11 female patients with coronary artery disease referred for cardiac evaluation during a 3 month period at the Royal Brompton National Heart & Lung Hospital, London. Patients were included in the study if they had a reproducible positive exercise test ($\geq 1$ mm of ST segment depression), proven coronary artery disease ($\geq 70\%$ diameter stenosis of one or more coronary arteries) and clinical indication of oestrogen deficiency. All but 2 of the women had 17β-oestradiol plasma concentrations lower than 200 pmol/l (normal postmenopausal plasma concentration <200 pmol/l). Patients with primary valvar congenital heart disease, myocardial or pericardial disease, congestive heart failure, left ventricular hypertrophy, ST segment changes at rest and left bundle branch block were excluded. Patients with uncorrected hypokalaemia and those receiving digitalis or antidepressant drugs were also excluded.

The mean age of the 11 female patients was 58±8 years. Angina had been present for 4.6±3 years. Previous myocardial infarction had occurred in 3 patients and 2 had undergone coronary artery bypass graft surgery. Hysterectomy had been performed in 2 patients. Eight patients were receiving β-blockers, 6 were receiving calcium channel antagonists and 4 were taking long acting nitrates. All patients underwent left ventriculography and selective coronary arteriography using the Judkins technique. Coronary artery disease (defined as at least 70% narrowing of the luminal diameter in one or more of the major coronary arteries or their major branches) was found in 3 vessels in 3 patients, in 2 vessels in 6 patients and in 1 vessel in 2 patients.

All 11 patients performed, off therapy, two exercise tests on two different days at the same hour of the day (±1 hour) using the modified Bruce protocol. Nitrates other than sublingual nitroglycerin were withdrawn 2 days before the study. Calcium channel blocking and β-adrenergic blocking agents were withdrawn 4 and 5 days before respectively. At least 6 hours elapsed between use of sublingual nitroglycerin and each exercise test. Forty minutes prior to each exercise, test patients were given either 17β-oestradiol (Estrace 1 mg, Mead Johnson laboratories, Evansville, Ind.) or 17β-oestradiol placebo (Mead Johnson laboratories, Evansville, Ind.) administered in random order. Both investigators and patients were blinded to the therapy taken by the patient. A complete 12-lead electrocardiogram was obtained at rest, every minute during the test, at the end of each stage, at the onset of 1 mm of planar ST segment depression, at peak exercise and every minute during recovery. Leads $V_2$, $V_5$ and II were continuously monitored. Systolic and diastolic blood pressure were measured at rest and monitored every minute during exercise and recovery.

A positive response in the electrocardiogram was defined as a horizontal or downsloping ST segment depression $\geq 1$ mm at 60 ms after the J point occurring at least in six consecutive complexes. The exercise test was concluded at the point of physical exhaustion, ST segment depression $\geq 3$ min, severe angina, severe dyspnoea or a decline in systolic blood pressure greater than 20 mm Hg. Total exercise time, time to myocardial ischaemia, heart rate, blood pressure at the onset of 1 min ST segment depression, maximal ST segment depression and the development of angina during exercise were recorded.

A blood sample for the evaluation of plasma levels of 17β-oestradiol was taken after each test and analyzed using a standard radioimmunoassay method.

The ST segment, 60 ms after the J point, was evaluated after signal averaging using a computer assisted system (CASE Marquette 12) in all 12 leads. The lead showing the greatest ST segment depression in the placebo exercise test was selected for analysis. Exercise tests were reviewed in random order by independent, experienced investigators blinded to the clinical data.

All patients developed chest pain on exertion after placebo, while only 6 patients experienced chest pain after 17β-oestradiol. All patients had at least 1 mm ST segment depression during the placebo exercise test, but only 7 patients had a positive exercise test after 17β-oestradiol. Blood pressure, heart rate and rate pressure product at rest, at the onset of 1 mm of ST depression and at peak exercise are shown in the following Table. Statistical significance was tested using the two-tailed Mann-Whitney Test. The data are expressed as mean (±ISD) and differences with 95% confidence intervals are given.

|  | Placebo (n = 11) mean (SD) | 17-β Oestradiol (n = 11) mean (SD) | p | Difference (n = 11) (95% Confidence Intervals) |
|---|---|---|---|---|
| Resting |  |  |  |  |
| Heart Rate [beats/min] | 75 (13) | 80 (12) | 0.08 | −5 (−10 to 0.2) |
| Blood Pressure [mm Hg] | 141 (23) | 132 (22) | 0.06 | 9 (−04 to 20) |
| Rate Pressure Product [mm Hg x (beats/min)] | 10681 (2810) | 10675 (3109) | 0.1 | 7 (−1163 to 1745) |
| 1 mm ST Depression |  |  |  |  |
| Heart Rate [beats/min] | 117 (18) | 124 (20)* | 0.02 | −10 (−15 to −5)* |
| Blood Pressure [mm Hg] | 164 (19) | 161 (20)* | 0.09 | −10 (−18 to 23)* |
| Rate Pressure Product [mm Hg x (beats/min)] | 19360 (4243) | 19897 (4410)* | 0.07 | −1600 (−3483 to 59)* |
| Time [seconds] | 456 (214) | 550 (166)* | 0.02 | −101 (−154 to −39)* |
| Peak Exercise |  |  |  |  |
| Heart Rate [beats/min] | 140 (34) | 139 (19) | 0.5 | 1 (−13 to 11) |
| Blood Pressure[mm Hg] | 165 (31) | 171 (20) | 0.7 | −6 (−21 to 30) |
| Rate Pressure Product [mm Hg x (beats/min)] | 22079 (5994) | 24010 (4662) | 0.3 | −1930 (−4265 to 2224 |
| Time [seconds] | 569 (249) | 658 (193) | 0.01 | −89 (−154 to −9) |
| Max ST Depression [mm] | 1.6 (0.4) | 1.2 (0.05) | 0.07 | −0.4 (0 to 0.7) | n = 7

It can be seen that the time to 1 mm ST segment depression (p<0.02) and total exercise time (p<0.01) were increased by 17β-oestradiol. Heart rate at the onset of 1 mm ST segment depression was increased by 17β-oestradiol (p<0.05). If the peak exercise time was substituted for the time to 1 mm ST segment depression in those 4 patients who did not achieve 1 mm ST segment depression on exercise after 17β-oestradiol, then time to 1 mm ST segment depression increased (p<0.004).

17β-oestradiol plasma concentrations increased from 155±168 to 2531±1192 pmol/l after administration of sublingual 17β-oestradiol (normal premenopausal physiological ranges; luteal 368 to 1100 pmol/l, midcycle 785 to 1840 pmol/l, follicular 74 to 368 pmol/l ). No patients reported any adverse symptoms after administration of either 17β-oestradiol or placebo.

In general, patients who responded to 17β-oestradiol had a low control plasma oestradiol concentration. The two patients with the smallest increase in time to 1 mm ST segment depression had higher plasma oestradiol concentrations.

In summary, patients were randomized to receive either sublingual 17β-oestradiol or placebo 40 minutes before a treadmill exercise test. Plasma 17β-oestradiol concentrations were confirmed to be higher after sublingual 17β-oestradiol when compared with sublingual placebo (2531±1192 vs 155±168 pmol/l, p<0.001). 17β-Oestradiol increased both time to 1 mm ST depression (449±158 vs 550±166 seconds, p<0.02, difference 101, 95% confidence intervals 39 to 154) and total exercise time (569±249 vs 658±193 seconds, p<0.01, difference 89, 95% confidence intervals 9 to 154). Heart rate and blood pressure were lower at rest after 17β-oestradiol (p<0.08). There were no differences in the haemodynamic variables either at the time of 1 mm ST segment depression or at peak exercise apart from the heart rate at 1 mm ST segment depression which was higher after 17β-oestradiol (p<0.02).

The results are similar to those obtained using acutely administered nitroglycerin or nitrates in patients with coronary artery diseases, and may explain some of the protection against coronary artery disease apparent in females before the menopause, and the protective effects of oestrogen replacement therapy in menopausal women.

Other embodiments and within the following claims.

What is claimed is:

1. A method for the treatment of myocardial ischaemia which results from coronary heart disease, which comprises administration to a patient of an effective amount of 17β-oestradiol.

2. The method of claim 1, wherein said patient is a post-menopausal woman.

3. A method of treatment of myocardial ischaemia which results from coronary heart disease, which comprises the steps of:

diagnosing coronary heart disease in a patient; and then administering to said patient an effective amount of 17β-oestradiol.

* * * * *

UNITED STATES PATENT AND TRADEMARK OFFICE
CERTIFICATE OF CORRECTION

PATENT NO. : 5,512,557
DATED      : April 30, 1996
INVENTOR(S): Peter Collins

It is certified that error appears in the above-identified patent and that said Letters Patent is hereby corrected as shown below:

On title page, after item "(22) Filed: Mar. 14, 1994", on the next line insert centered heading
--Related Foreign Application Data--
and on the next line
--Priority claimed from Great Britain Patent 9314695.9 filed July 15, 1993.--

Signed and Sealed this

Twenty-fifth Day of February, 1997

Attest:

Attesting Officer

BRUCE LEHMAN

Commissioner of Patents and Trademarks